(12) United States Patent
Yamamoto et al.

(10) Patent No.: US 8,093,203 B2
(45) Date of Patent: *Jan. 10, 2012

(54) METHOD OF ENHANCING FRAGRANCE BY ADDING OPTICALLY ACTIVE MUSCONE COMPOSITION

(75) Inventors: Kenichi Yamamoto, Kanagawa (JP); Misao Yagi, Kanagawa (JP); Hiroyuki Matsuda, Kanagawa (JP); Kenji Maruyama, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 793 days.

This patent is subject to a terminal disclaimer.

(21) Appl. No.: 11/719,109

(22) PCT Filed: Nov. 12, 2004

(86) PCT No.: PCT/JP2004/016825
§ 371 (c)(1),
(2), (4) Date: May 11, 2007

(87) PCT Pub. No.: WO2006/051597
PCT Pub. Date: May 18, 2006

(65) Prior Publication Data
US 2009/0143485 A1 Jun. 4, 2009

(51) Int. Cl.
*A61Q 13/00* (2006.01)
*A61K 31/12* (2006.01)
*A61K 47/00* (2006.01)
*A61K 8/02* (2006.01)

(52) U.S. Cl. ............. 512/8; 514/690; 514/772; 424/401

(58) Field of Classification Search .................. None
See application file for complete search history.

(56) References Cited

U.S. PATENT DOCUMENTS
2003/0054049 A1* 3/2003 Shoji et al. .................... 424/733

FOREIGN PATENT DOCUMENTS
JP 7-324196 12/1995

OTHER PUBLICATIONS

Tanaka et al., "Catalytic Enantioselective Conjugate Addition of Chiral Alkoxydimethylcuprate to (E)-Cyclopentadec-2-enone," J. Chem. Soc. Perkin Trans. 1, 1992, pp. 1193-1194.*

Fujimoto et al., "Synthesis of (R)- and (S)-Muscone," Biosci. Biotechnol. Biochem., 2002, 66 (6), pp. 1389-1392.*

Scafato, et al., "Catalytic enantioselective conjugate addition of dialkyl zinc reagents to . . ." Tetrahedron: Asymmetry, vol. 14, No. 24 (2003) 3873-77.

Yamamoto, et al., "A novel synthetic method for (R)- and (S)-muscones by enantioselective hydrogenation of . . . complexes" Tetrahedron: vol. 58, No. 45 (2002) 9209-12.

Alexakis et al., "Catalytic Asymmetric Conjugate Addition on Macrocyclic and Acyclic Enones. Synthesis of R-(-)-Muscone", Synlett, No. 11 (1999) 1811-13 (XP002551044).

Tanaka, et al., "Asymmetric Synthesis of (R)-Muscone by Enantioselective Addition of Chiral Methyl Cuprate to (E)-2-Cyclopentadecen-1-one", Journal of the Chemical Society, No. 11 (1990) 795-97 (XP000128349).

Ogawa, et al., "Asymmetric Syntheses of (R)-(-)-Muscone based on Diastereoselective Conjugate Addition", Journal of the Chemical Society, No. 20 (1991) 1438-1439 (XP000233923).

Gousei Kouryou, Kagaku to Syouhin Chishiki, (Synthetic Aromachemicals, Chemistry and Merchandise Knowledge) pp. 492-497, written by Motoichi Indoh, published Mar. 6, 1996, from The Chemical Daily Co., Ltd.

Gosei Kouryou no Saisin Gijutsu (The Recently Techniques on Synthetic Aromachemicals) pp. 72-90, published by CMC Publishing Co., Ltd., 1982.

Scafato, et al., "Asymmetric activation of tropos catalysts in the stereoselective . . . ", Tetrahedron, vol. 60, No. 40 (2004), pp. 8801-8806.

Iuliano, et al., "Deoxycholid acid-based phosphites as chiral ligands in the enantioselective . . . ", Tetrahedron: Asymmetry, vol. 15, No. 16 (2004), pp. 2533-2538.

* cited by examiner

*Primary Examiner* — Sreeni Padmanabhan
*Assistant Examiner* — Jody Karol
(74) *Attorney, Agent, or Firm* — Fitzpatrick, Cella, Harper & Scinto

(57) ABSTRACT

The object of the invention relates to a development of a new musk-feeling fragrance material which is a highly scenting musk-feeling fragrance, and is to provide a fragrance composition which, when added to fragrances or cosmetics, can improve the fixative property and express a high performance and excellent musky aromatic quality.

A fragrance composition is prepared using, as the active ingredient, a mixture of (R)-form of optically active muscone with (S)-form of optically active muscone with the mixing ratio thereof within the range of from 90:10 to 95:5 (weight ratio) in terms of weight ratio, or a mixture of (R)-form of optically active muscone with (S)-form of optically active muscone with the mixing ratio thereof within the range of from 75:25 to 80:20 (weight ratio) in terms of weight ratio.

4 Claims, No Drawings

METHOD OF ENHANCING FRAGRANCE BY ADDING OPTICALLY ACTIVE MUSCONE COMPOSITION

TECHNICAL FIELD

The present invention relates to a novel optically active muscone composition, a fragrance composition and a fragrance enhancer for fragrances or cosmetics containing the same, and fragrances or cosmetics containing the same. More particularly, the invention relates to a novel optically active muscone composition which gives a musk-feeling fragrance excellent in a diffusiveness and a voluminousness or a powderiness, a novel musk-feeling fragrance composition and a fragrance enhancer for fragrances or cosmetics with which high performance fragrances or cosmetics having excellent odor can be obtained by improving odor and aromatic quality (to be referred sometimes to as aromatic quality hereinafter) of fragrances or cosmetics, and fragrances or cosmetics containing the musk-feeling fragrance composition or the fragrance enhancer for fragrances or cosmetics. The invention further relates to the use of the novel optically active muscone composition.

BACKGROUND ART

In recent years, accompanied by the diversification of various food materials, food additives, foods or beverages (including articles of taste), fragrances or cosmetics, sanitation materials, sundries, pharmaceuticals and the like, new demands for a fragrance to be used therein have been increasing, and concerns have been directed toward the development of aromatic materials having a highly-scenting unique odor. Also, with the recent uprush of the nature-oriented style of people and also from the safety point of view, great concerns have been directed toward the development of new aromatic materials derived from natural compounds, or identical or similar to the natural compounds, with regard to highly-scenting musk-feeling fragrances by which the natural environment can be imaged characteristically.

On the other hand, muscone as a typical example of the musk-feeling fragrances is the main aromatic component of natural musk, and contained in an amount of approximately from 0.5 to 2.0% in the natural musk. Muscone was discovered by Walbaum in 1906, and its chemical structure was determined by Ruzicka in 1926 as 3-methylcyclopentadecanone.

By the efforts of a large number of researchers thereafter, presently it is known that the natural muscone is (−)-(R)-3-methylcyclopentadecanone; that muscone is now on the market and can therefore be easily obtained because of the establishment of chemical synthesis method of muscone; that the synthesized article is a racemic form as a mixture of l-form and d-form of muscone; that the l-form and d-form of muscone obtained by optical resolution, namely (−)-(R)-form and (+)-(S)-form, can be obtained from the racemic form; that the optically active muscone can also be synthesized making use of an asymmetric synthesis; that when odors of the (−)-(R)-form and (+)-(S)-form are compared, the (R)-form has a strong musky odor having diffusiveness (threshold: 3 ppm), while the (S)-form has a chemical, spread-less and poor weak musky odor (threshold: 10 ppm) and, as a result, the (R)-form is about 3 times larger than the (S)-form regarding the strength of smell, and the like (e.g., see Non-patent Reference 1 and Non-patent Reference 2).

Based on the superior aromatic quality and the like of (−)-(R)-muscone, there is a report, for example, on a fragrance composition which can keep a highly-scenting odor for a prolonged period of time, in which at least one species selected from androstenols and 3-methyl-2-hexenoic acid is allowed to be coexistent with (−)-(R)-muscone (Patent Reference 1).

However, the muscone conventionally used in fragrances or cosmetics is (−)-(R)-muscone or a racemic form as an equivalent mixture of (R)-form and (S)-form of muscone.

Patent Reference 1: JP-A-7-324196

Non-patent Reference 1: "Gousei Kouryou, Kagaku to Syouhin Chishiki, (Synthetic Aromachemicals, Chemistry and Merchandise Knowledge)" pp. 492-497, written by Motoichi Indoh, published Mar. 6, 1996, from The Chemical Daily Co., Ltd.

Non-patent Reference 2: "Gosei Kouryou no Saisin Gijutsu (The Recently Techniques on Synthetic Aromachemicals)" pp. 72-90, published by CMC Publishing CO., LTD., 1982

DISCLOSURE OF THE INVENTION

Problems that the Invention is to Solve

An object of the invention relates to the development of a new fragrance material which is a highly-scenting musk-feeling fragrance material, and is to provide a fragrance composition and a fragrance enhancer for fragrances or cosmetics, which, when added to the fragrances or cosmetics, can improve their fixative property and express a high performance and excellent musky aromatic quality having a diffusiveness and a voluminousness or a powderiness. It is also to provide a fragrance composition for fragrances or cosmetics, which comprises the fragrance composition and fragrance enhancer for fragrances or cosmetics. In addition, another object of the invention is to provide fragrances or cosmetics which show improved fixative property and have a high performance and musky aromatic quality excellent in diffusiveness and voluminousness or powderiness. It is also to provide a composition which produces the fragrance composition and fragrance enhancer for fragrances or cosmetics.

Means for Solving the Problems

As a result of intensive studies carried out with the aim of achieving the aforementioned objects, the present inventors have found that, surprisingly, a fragrance obtained by mixing the (R)-form and (S)-form of an optically active muscone at a specific ratio has a highly scenting musk performance odor which is particularly excellent in diffusiveness and voluminousness, and also has a highly scenting musk performance odor which is particularly excellent in powderiness.

That is, it is found that an optically active muscone in which the configuration of methyl group is within a ratio (weight ratio) of from 90:10 to 95:5 as a mixing ratio of (R)-form/(S)-form, which is different from the muscone so far used as a fragrance, particularly the (−)-(R)-muscone, and cannot be obtained easily from those derived from a natural product, has a highly scenting musk performance odor which is particularly excellent in diffusiveness and voluminousness; and an optically active muscone in which the configuration of methyl group is within a ratio (weight ratio) of from 75:25 to 80:20 as a mixing ratio of (R)-form/(S)-form has a highly scenting musk performance odor which is particularly excellent in diffusiveness and powderiness. As a result, it is found that when the aforementioned (R)-form/(S)-form mixture of optically active muscone having a specific ratio is added solely, or is added to fragrances or cosmetics after diluting it with DPG or the like solvent or in the form of a fragrance composition prepared by mixing it with other fragrance component, the fixative property is improved, and an excellent high performance musky odor excellent in diffusiveness and voluminousness or powderiness is expressed in fragrances or cosmetics. Based on such findings, studies were further continued to thereby finally accomplish the invention.

Namely, the present invention is an optically active muscone composition, which comprises (R)-form of optically active muscone and (S)-form of optically active muscone mixed with a mixing ratio within a range of from 75:25 to 95:5 in terms of weight ratio.

The present invention is the optically active muscone composition according to claim 1, which comprises (R)-form of optically active muscone and (S)-form of optically active muscone mixed with a mixing ratio within a range of from 75:25 to 95:5 in terms of weight ratio, said composition being useful as a fragrance composition and a fragrance enhancer for fragrances or cosmetics.

The present invention is the optically active muscone composition wherein the mixing ratio of (R)-form of optically active muscone and (S)-form of optically active muscone is within a range of from 90:10 to 95:5 in terms of weight ratio.

The present invention is the optically active muscone composition wherein the mixing ratio of (R)-form of optically active muscone and (S)-form of optically active muscone is within a range of from 75:25 to 80:20 in terms of weight ratio.

The present invention is a fragrance composition, which comprises an optically active muscone composition containing (R)-form of optically active muscone and (S)-form of optically active muscone with a mixing ratio within a range of from 90:10 to 95:5 in terms of weight ratio, or an optically active muscone composition containing (R)-form of optically active muscone and (S)-form of optically active muscone with a mixing ratio within a range of from 75:25 to 80:20 in terms of weight ratio.

The present invention is a fragrance enhancer for fragrances or cosmetics, which comprises an optically active muscone composition containing (R)-form of optically active muscone and (S)-form of optically active muscone with a mixing ratio within a range of from 90:10 to 95:5 in terms of weight ratio, or an optically active muscone composition containing (R)-form of optically active muscone and (S)-form of optically active muscone with a mixing ratio within a range of from 75:25 to 80:20 in terms of weight ratio.

The present invention is use of the optically active muscone composition for imparting a musky odor to fragrances or cosmetics.

The present invention is use of the optically active muscone composition as a fragrance enhancer for fragrances or cosmetics.

The following describes the invention in detail.

The optically active muscone composition according to the invention is constituted of two species of optically active muscone, namely (−)-(R)-3-methylcyclopentadecanone (to be referred sometimes to as (R)-muscone or (R)-form hereinafter) and (+)-(S)-3-methylcyclopentadecanone (to be referred sometimes to as (S)-muscone or (S)-form hereinafter).

According to the invention, when these optically active muscone is prepared in such a manner that the (R)-form/(S)-form mixing ratio (weight ratio) is set within the range of from 75:25 to 95:5, it shows an aromatic quality superior to that of the conventionally and frequently used muscone fragrance. Particularly, a composition obtainable by adjusting the optically active muscone to have the (R)-form/(S)-form mixing ratio weight ratio) of within the range of from 90:10 to 95:5 or from 75:25 to 80:20, shows an aromatic quality which is particularly superior to that of the conventional muscone fragrance.

That is, when a mixture obtainable by mixing (R)-muscone and (S)-muscone at a ratio of from 90:10 to 95:5 in terms of weight ratio, or both of them at a ratio of from 75:25 to 80:20, is used as a fragrance composition, this fragrance composition becomes a markedly excellent fragrance composition which has excellent aromatic quality, particularly musky aromatic quality, than that of the conventionally and frequently used muscone fragrance, is excellent in diffusiveness and voluminousness and powderiness, and can give wholly positive effects.

The methods for using and applying the aforementioned fragrance composition are not particularly limited, can be applied to all of the conventional methods for using and applying fragrance, and can provide excellent aromatic quality. In addition, the use of such an optically active muscone mixture as a fragrance enhancer for fragrances or cosmetics is also one of the characteristics of the invention. The fragrance enhancer for fragrances or cosmetics as used herein means a fragrance or a fragrance composition, which has a function to markedly improve a musky aromatic quality of fragrances or cosmetics or a fragrance for fragrances or cosmetics when a small amount thereof is added to or mixed with these fragrances or cosmetics or fragrance for fragrances or cosmetics.

Regarding the starting material for preparing the aforementioned (R)-form/(S)-form mixture of optically active muscone, those which are extracted from natural substances can be used, or those which are obtainable by a chemical synthesis method can also be used.

Since most of those which are extracted from natural substances are (R)-muscone, they can be used as the (R)-form of the aforementioned starting material. However, since its obtainable amount is very small, it is desirable to use those which are prepared using a chemical synthesis method in order to obtain the aforementioned starting material in a large amount. For example, (R)-form and (S)-form of optically active muscone can be obtained by preparing a racemic form as an (R)-form/(S)-form mixture of optically active muscone, and then using an optical resolution method. In addition, as a different method, (R)-form and (S)-form of optically active muscone can be prepared, for example, by carrying out asymmetric hydrogenation of 3-methyl-2-cyclopentadecene-1-one using (R)-form or (S)-form of a ruthenium-optically active phosphine complex as the catalyst.

Subsequently, using the (R)-muscone or (S)-muscone as the material and mixing them to have a desired ratio, the optically active muscone composition of the invention can be obtained, and the fragrance composition and fragrance enhancer for fragrances or cosmetics of the invention can also be obtained.

In this connection, since the muscone obtained from a natural material is (R)-muscone, a method in which (S)-muscone obtained by a chemical synthesis method is added to or mixed with the (R)-muscone derived from a natural source at a desired ratio is also effective. In the same manner, a racemic form muscone can be added to or mixed with the aforementioned (R)-muscone at a desired ratio In addition, a mixture in which (R)-muscone and (S)-muscone are mixed at a desired ratio can also be prepared by optionally controlling reaction conditions and the like of the aforementioned optical resolution method and asymmetric synthesis method.

As shown in the following examples, the mixture of (R)-form and (S)-form of the optically active muscone of the invention is markedly good in terms of the aromatic quality and odor strength. Also, since the mixture of (R)-form and (S)-form of the optically active muscone of the invention has a highly-scenting excellent musky peculiar strong odor characteristic and also has significant odor durability, a highly scenting fragrance composition can be provided by blending this mixture. In addition, when the mixture of (R)-form and (S)-form of the optically active muscone of the invention is blended, acting effects of the desired odor duration and residual odor are particularly improved.

The mixture of (R)-form and (S)-form of the optically active muscone of the invention has a musky aromatic quality by itself. In addition, the mixture can be used as an enhancer. Amount of the mixture to be blended with a fragrance or a fragrance composition varies depending on the kinds of the fragrance and formulated fragrance and the purpose, but in general, a blending amount, for example, of from 0.0001 to 10% by weight, particularly from 0.001 to 5% by weight, further preferably from 0.01 to 1% by weight, based on the fragrance or the fragrance composition is suitable. The aforementioned fragrance or the fragrance composition to which the mixture of the invention is added or mixed is not particularly limited.

A fragrance composition for fragrances or cosmetics can be prepared by further adding a generally used fragrance component to the aforementioned mixture of (R)-form and (S)-form of the optically active muscone. As the other fragrance to be added and used, various types of synthetic aromachemical, natural essential oil, natural aromachemical, citrus fruit oil, animal aromachemical and the like can be exemplified. For example, a broad range of fragrance components described in the following reference can be used.

Typical examples of these fragrances include α-pinene, limonene, cis-3-hexenol, phenylethyl alcohol, styralyl acetate, eugenol, rose oxide, linalool, benzaldehyde, methyl dihydrojasmonic acid, and Thesaron (manufactured by Takasago International Corporation). In addition, the flavors and fragrances described in Arctander S., "Perfume and Flavor Chemicals", published by the author, Montclair, N.J. (U.S.A.), 1969, can also be exemplified.

When the aforementioned mixture of (R)-form and (S)-form of the optically active muscone is added, for example, to bergamot oil, galbanum oil, lemon oil, geranium oil, lavender oil, mandarin oil or the like natural essential oil, a novel fragrance composition for fragrances or cosmetics, in which the odor and aromatic quality originally possessed by the natural essential oil are improved in terms of mildness, richness, freshness and high tasting, and diffusivity and holding ability thereof are enhanced, can be prepared.

According to the invention, one or two or more of generally used other fragrance fixative agents may be added to the aforementioned mixture of (R)-form and (S)-form of the optically active muscone or the fragrance composition for fragrances or cosmetics, and for example, ethylene glycol, propylene glycol, dipropylene glycol, glycerol, hexyl glycol, benzyl benzoate, triethyl citrate, diethyl phthalate, Hercolyn (methyl abietate), middle-chain fatty acid triglyceride and the like may be used in combination therewith.

The fragrances or cosmetics which can be scented using the mixture of (R)-form and (S)-form of the optically active muscone of the invention or a fragrance composition comprising the compounds are not particularly limited, and for example, fragrance products, skin-care cosmetics, make-up cosmetics, hair cosmetics, anti-sunburn cosmetics, medicinal cosmetics, hair-care products, soap, body lotions, bath liquids, detergents, soft finishing agents, cleaners, kitchen detergents, bleaching agents, aerosol agents, deodorant-aromatics, sundries and the like can be cited.

Various forms thereof can be exemplified, such as perfumed water, Eau de Perfum, Eau de toilette, Eau de cologne and the like as the aforementioned fragrance products; face washing cream, vanishing cream, cleansing cream, cold cream, massage cream, milky lotion, toilette lotion, beauty wash, pack, make remover and the like as the as the aforementioned skin-care cosmetics; foundation, face powder, pressed powder, talcum powder, rouge, lipstick, lip cream, cheek rouge, eye liner, mascara, eye shadow, eyebrow-color, eye pack, nail enamel, enamel remover and the like as the as the aforementioned make-up cosmetics; pomade, brilliantine, set lotion, hair stick, hair solid, hair oil, hair treatment, hair cream, hair tonic, hair liquid, hair spray, bandlin, hair growth agent, hair dye and the like as the as the aforementioned hair cosmetics; suntan product, sun screen product and the like as the as the aforementioned anti-sunburn cosmetics; antiperspirant, after-shaving lotion and gel, permanent wave agent, medicinal soap, medicinal shampoo, medicinal skin cosmetics and the like as the as the aforementioned medicinal cosmetics; shampoo, rinse, rinse-in-shampoo, conditioner, treatment, hair pack and the like as the as the aforementioned hair-care products; toilet soap, bath soap, scented soap, transparent soap, synthetic soap and the like as the as the aforementioned soap; body soap, body shampoo, hand soap, face cream and the like as the as the aforementioned body lotions; bath agent (bath salt, bath tablet, bath liquid or the like), foam bath (bubble bath or the like), bath oil (bath perfume, bath capsule or the like), milk bath, bath jerry, bath cube and the like as the as the aforementioned bath liquids; heavy detergent for clothing, light detergent for clothing, liquid detergent, laundry soap, compact detergent, powder soap and the like as the as the aforementioned detergents; softener, furniture care and the like as the as the aforementioned soft finishing agents; cleanser, house cleaner, toilet cleaner, bath cleaner, glass cleaner, mold remover, waste pipe cleaner and the like as the as the aforementioned cleaners; kitchen soap, kitchen synthetic soap, tableware detergents and the like as the as the aforementioned kitchen detergents; oxidation type bleaching agent (a chlorine base bleaching agent, oxygen base bleaching agent or the like), reduction type breaching agent (sulfur base bleaching agent or the like), optical bleaching agent and the like as the as the aforementioned bleaching agents; spray-type aerosols, powder spray and the like as the as the aforementioned aerosol agents; solid-type, gel-type, liquid-type (aqueous or oily) and the like counterparts as the aforementioned deodorant-aromatics; and tissue paper, toilette paper and the like as the as the aforementioned sundries.

Product shape of the aforementioned (R)-form/(S)-form mixture of optically active muscone may be the shape of the mixture itself, but as other shapes, optional shapes are selected and used, such as, for example, liquid shapes dissolved in alcohols, propylene glycol, glycerol, dipropylene glycol and the like polyhydric alcohols or triethyl citrate, benzyl benzoate, diethyl phthalate and the like esters; gum Arabic, tragacanth gum and the like natural gummy matters; emulsion shapes emulsified with glycerol fatty acid ester, sucrose fatty acid ester or the like emulsifier; powder shapes coated using gum Arabic and the like gummy matters, gelatin, dextrin and the like fillers; soluble or dispersion shapes solubilized or dispersed using a surfactant such as nonionic surfactant, anionic surfactant, cationic surfactant, ampholytic surfactant or the like; or microcapsules obtained by treating with an encapsulation agent.

In addition, the aforementioned fragrance composition may be used by stabilizing it and providing it with sustained release property, through its enclosure with cyclodextrin or the like inclusion agent. These may be used by optionally selecting suitable shape of the final product, such as liquid shape, solid shape, powder shape, gel shape, mist shape, aerosol shape or the like.

In this connection, amount of the aforementioned (R)-form/(S)-form mixture of optically active muscone, or a fragrance composition for fragrances or cosmetics, to be added to a fragrance product or the like final product is optionally changed according to the object to be used, conditions, expected effect and action and the like of each product and therefore cannot be determined, but is generally from about 0.00001 to about 20% by weight.

Advantage of the Invention

The optically active muscone composition having a specified range of (R)-form/(S)-form ratio of the aforementioned optically active muscone has an excellent odor having high performance and can be said to have characteristics which are superior to those of the conventionally known musk-feeling fragrance. Since the (R)-form/(S)-form mixture of optically active muscone to be used in the invention exerts its effects even at a small amount, it renders possible scenting of fragrances or cosmetics which require scenting with a fragrance, and its aromatic quality peculiar to musk and excellent in diffusiveness, voluminousness and powderiness can give broadening and settlement to a formulated fragrance containing the same and thereby can improve its aroma and strength, so that it can provide wholly positive effects and can give fresh and creamy musky feeling. Since (S)-muscone has a chemical and broadening-less poor and weak musk odor, it cannot provide suitable odor. In addition, even in the case of mixtures of (R)-muscone and (S)-muscone, a mixture having an (R)-form/(S)-form mixing ratio outside of the limited range of ratio of from 90:10 to 95:5 or from 75:25 to 80:20 (weight ratio) has poor odor performance and odor strength, so that its effects cannot be said sufficient.

Thus, the optically active muscone composition of the invention having specified range of (R)-form/(S)-form ratio is particularly superior to the conventional musk-feeling fragrances and therefore is a markedly practical invention.

BEST MODE FOR CARRYING OUT THE INVENTION

Examples

The followings illustratively describe the invention with reference to inventive examples, synthesis examples, comparative examples and application examples, but the invention is not restricted thereto and may be changed within such a range that it does not overstep the scope of the invention. In this connection, regarding the unit of the formulations described in the followings, % means % by weight unless otherwise noted.

Synthesis Example 1

Synthesis of 2,15-hexadecanedione

A 1 liter capacity four neck flask equipped with a condenser, a thermometer, a dropping funnel and a stirring device was charged with 31.7 g (1.32 mol) of sodium hydride and 500 ml of tetrahydrofuran (THF). While stirring the mixture, 172 g (1.32 mol) of ethyl acetoacetate was added dropwise thereto spending 3 hours.

Next, under reflux, 100 g (0.33 mol) of 1,10-dibromodecane was added dropwise thereto spending 4 hours, and then this was stirred for 12 hours to complete the reaction. The reaction liquid was cooled down to room temperature and mixed with 400 ml of 5% hydrochloric acid solution, and the organic layer and water layer were separated. The thus obtained organic layer was subjected to washing and phase separation twice using saturated brine, and THF in this organic layer was evaporated under a reduced pressure using an evaporator to obtain 160 g of a concentrated oil.

A 160 g portion of this concentrated oil and 528 g of 10% sodium hydroxide aqueous solution were put into a flask equipped with a condenser and stirred at room temperature. After 8 hours of stirring at the same temperature, 129 g of 50% sulfuric acid solution was added thereto to carry out reflux. The reaction was completed by stirring for 3 hours, and the reaction liquid was returned to room temperature. The reaction liquid was filtered using a Buchner funnel to obtain 40 g of crude crystals. By recrystallizing the crude crystals using ethanol, 38 g (0.15 mol) of 2,15-hexadecanedione was obtained at a yield of 45% of the theoretical amount. Melting point of this substance was 83 to 84° C.

Synthesis Example 2

Synthesis of (E)- and (Z)-3-methyl-cyclopentadecene-1-one

A 2 liter capacity four neck flask equipped with a condenser, a thermometer, a dropping funnel and a stirring device was subjected to nitrogen replacement, charged with 400 ml of THF and 8.2 g (88 mmol) of phenol and cool to 0° C., and then 80 ml of 1 M diisopropyl aluminum hydride hexane solution (80 mmol) was added dropwise thereto. After the dropwise addition and subsequent returning to room temperature, 7.6 g (96 mmol) of pyridine and 1.6 liters of n-hexane were added thereto and then increased to 65° C. to carry out reflux.

Next, a mixed solution of 400 ml THF and 40.0 ml of n-hexane containing 5 g (20 mmol) of 2,15-hexadecanedion obtained in Synthesis Example 1 was added dropwise thereto under reflux spending 11 hours, and further stirred for 2 hours after completion of the dropwise addition. After completion of the reaction and subsequent returning to room temperature, 3 N hydrochloric acid was added thereto to separate the organic layer and water layer, the organic layer was washed with 5% sodium hydroxide aqueous solution and subjected to washing and phase separation twice using saturated brine, and THF in the thus obtained organic layer was evaporated under a reduced pressure using an evaporator to obtain a concentrated oil.

When this concentrated oil was purified by a silica gel column chromatography, 2.7 g (11.4 mmol) of an aldol mixture of 3-methyl-cyclopentadecene-1-one and (E)- and (Z)-3-methyl-cyclopentadecene-1-one was obtained. By further purifying this aldol mixture by a silica gel column chromatography, 0.7 g (3.0 mmol) of (E)-3-methyl-cyclopentadecene-1-one was obtained. Also, by purifying using a column chromatography with silver nitrate-coated silica gel, 0.5 g (2.1 mmol) of (Z)-3-methyl-cyclopentadecene-1-one was obtained.

Synthesis Example 3

Synthesis of (R)-muscone

The atmosphere in a 100 ml capacity autoclave was replaced by nitrogen, and then 2.3 g (9.7 mmol) of (E)-3-methyl-cyclopentadecene-1-one obtained by the method of Synthesis Example 2, 9 mg (0.005 mmol) of Ru$_2$Cl4[(S)-Tol-BINAP]$_2$NEt$_3$ and 10 ml of methanol were charged therein and allowed to undergo the reaction at 25° C. for 24 hours under a hydrogen pressure of 5.07×10$^6$ Pa. After completion of the reaction, the solvent was evaporated under a reduced pressure, and the thus obtained crude product was purified by a silica gel column chromatography (hexane:ethyl acetate = 20:1 (volume ratio)) to obtain 2.2 g (yield 95%) of optically almost pure (R)-muscone.

Specific rotation $[\alpha]_D^{25}$ of the thus obtained (R)-muscone was −12.0° (C=1.20, methanol). In this connection, specific rotation $[\alpha]_D^{25}$ of the (R)-muscone described in a reference (Helv. Chim. Acta, vol. 60, 1977, p. 925) is −11.7° (C=0.80, methanol).

Synthesis Example 4

Synthesis of (R)-muscone

The atmosphere in a 100 ml capacity autoclave was replaced by nitrogen, and then 2.3 g (9.7 mmol) of (Z)-3-methyl-cyclopentadecene-1-one obtained by the method of Synthesis Example 2, 9 mg (0.005 mmol) of Ru$_2$Cl$_4$[(R)-Tol-BINAP]$_2$NEt$_3$ and 10 ml of methanol were charged therein and allowed to undergo the reaction at 25° C. for 24 hours under a hydrogen pressure of 5.07×10$^6$ Pa. After completion of the reaction, the solvent was evaporated under a reduced pressure, and the thus obtained crude product was purified by a silica gel column chromatography (hexane:ethyl acetate = 20:1 (volume ratio)) to obtain 2.2 g (yield 95%) of optically almost pure (R)-muscone.

Specific rotation $[\alpha]_D^{25}$ of the thus obtained (R)-muscone was −11.9° (C=1.10, methanol).

Synthesis Example 5

Synthesis of (S)-muscone

The atmosphere in a 100 ml capacity autoclave was replaced by nitrogen, and then 2.3 g (9.7 mmol) of (Z)-3-methyl-cyclopentadecene-1-one obtained by the method of Synthesis Example 2, 0.9 mg (0.0005 mmol) of Ru$_2$Cl$_4$[(S)-BINAP]$_2$NEt$_3$ and 10 ml of methanol were charged therein and allowed to undergo the reaction at 75° C. for 30 hours under a hydrogen pressure of 5.07×10$^6$ Pa. After completion of the reaction, the solvent was evaporated under a reduced pressure, and the thus obtained crude product was purified by a silica gel column chromatography (hexane:ethyl acetate = 20:1 (volume ratio)) to obtain 2.2 g (yield 95%) of optically almost pure (S)-muscone.

Specific rotation $[\alpha]_D^{25}$ of the thus obtained (S)-muscone was +11.7° (C=1.10, methanol).

Inventive Example 1

Evaluation of Odor Quality

Regarding the samples prepared by mixing the optically active muscone products obtained in Synthesis Examples at optional ratios, respective samples were put on bottle mouths and filter papers to carry out the sensory evaluation by the perfumers having an experience in this field of 5 years or more. The evaluation results are shown in Table 1.

TABLE 1

| Compound name | Odor |
|---|---|
| R alone | Clean musk |
| R:S = 97.5:2.5 (95% ee) | Clean musk |
| R:S = 95:5 (90% ee) | Highly scenting musk particularly excellent in diffusiveness and voluminousness, it has natural richness |
| R:S = 92.5:7.5 (85% ee) | Highly scenting musk particularly excellent in diffusiveness and voluminousness, it has natural richness |
| R:S = 90:10 (80% ee) | Highly scenting musk particularly excellent in diffusiveness and voluminousness, it has natural richness |
| R:S = 87.5:12.5 (75% ee) | Flat musk |
| R:S = 85:15 (70% ee) | Flat musk |
| R:S = 82.5:17.5 (65% ee) | Flat musk |
| R:S = 80:20 (60% ee) | Highly scenting musk particularly excellent in powderiness, it has cleanness and softness |
| R:S = 77.5:22.5 (55% ee) | Highly scenting musk particularly excellent in powderiness, it has cleanness and softness |
| R:S = 75:25 (50% ee) | Highly scenting musk particularly excellent in powderiness, it has cleanness and softness |
| R:S = 72.5:27.5 (45% ee) | Flat and weak musk |
| R:S = 50:50 (0% ee) | Flat and weak musk |

In the Table 1, R means (R)-muscone and S means (S)-muscone.

A musk-feeling fragrance is the most important composing element of the formulated fragrance, and effect of the musk-feeling fragrance is not only its contribution to odor as a single substance, but also its great influence upon the whole odor, for example, like the case of the odor of formulated fragrance. A musk-feeling having superior diffusiveness and voluminousness or powderiness can give broadening and settlement to a formulated fragrance containing the same and thereby can improve its aroma and strength, so that it can provide wholly positive effects. On the other hand, a simply clean or flat musk fragrance cannot provide wholly positive effects and cannot improve aroma and strength.

That is, in the case of a musk-feeling fragrance, it is necessary not only to have a simple clean or flat musk odor but also an aromatic quality having excellent diffusiveness and voluminousness or powderiness, for exerting the excellent aromatic quality specific to musk.

As is evident from the above, the (R)-form/(S)-form mixture of optically active muscone of the invention has an odor having particularly high taste and musk-specific performance, within a limited range of their ratios of from 90:10 to 95:5 and from 75:25 to 80:20.

Inventive Example 2

Production of Fragrance Composition for Shampoo

A fragrance composition for shampoo was prepared in the usual way based on the following formulation.

Formulation Example 1

| Components | Parts by weight |
| --- | --- |
| Benzyl salicylate | 55 |
| L-citronellol | 10 |
| Ethyl acetoacetate | 5 |
| Galaxolide 50 BB* (mfd. By IFF) | 390 |
| Geraniol | 10 |
| Hedione (mfd. by Firmenich) | 120 |
| Helliobouquet (mfd. by Takasago International Corporation) | 8 |
| Cis-3-hexen-1-ol 10% DPG** solution | 10 |
| Cis-3-hexenyl acetate 10% DPG solution | 5 |
| Hexyl cinnamic aldehyde | 50 |
| β-Ionone | 17 |
| Kovanol (mfd. by Takasago International Corporation) | 40 |
| Lemon oil | 40 |
| Linalool | 45 |
| Linalyl acetate | 45 |
| Nerolidol | 55 |
| Phenylethyl alcohol | 30 |
| Phenylethyl cinnamate | 5 |
| Santalex T (mfd. by Takasago International Corporation) | 35 |
| Triplal 10% DPG solution (mfd. by IFF) | 5 |
| Maltol 1% DPG solution | 15 |
| (R)-form/(S)-form (92.5:7.5) mixture of optically active muscone | 5 |
| Total | 1000 |

*BB means benzyl benzoate, and
**DPG means dipropylene glycol.

Inventive Example 3

A fragrance composition for shampoo was prepared by the same formulation of Inventive Example 2, except that an (R)-form/(S)-form (77.5:22.5) mixture of optically active muscone was used instead of the (R)-form/(S)-form (92.5:7.5) mixture of optically active muscone in the formulation of Inventive Example 2.

Comparative Example 1

A fragrance composition was prepared by the same formulation of Inventive Example 2, except that (R)-muscone (100%) was used instead of the (R)-form/(S)-form (92.5:7.5) mixture of optically active muscone in the formulation of Inventive Example 2.

Application Example 1

Production of Shampoo

Using the fragrance compositions for shampoo prepared in Inventive Example 2, Inventive Example 3 and Comparative Example 1, shampoos were prepared by stirring the following components at 80° C. until they became uniform, and then cooling to 35° C.

Shampoo composition

| Components | Part(s) by weight |
| --- | --- |
| Sodium lauryl sulfate | 40.00 |
| N-Coconut oil fatty acid acyl-N-carboxymethoxyethyl-N-carboximethyl ethylenediamine disodium | 10.00 |
| Coconut oil fatty acid diethanolamide (2) | 2.00 |
| Butylene glycol | 2.00 |
| Citric acid | 0.35 |
| Sodium chloride | 0.10 |
| Methyl paraben | 0.20 |
| Propyl paraben | 0.10 |
| Tetrasodium edetate | 0.10 |
| Fragrance composition* | 0.50 |
| Purified water | balance |
| Total | 100 |

*The fragrance composition of Inventive Example 2, Inventive Example 3 or Comparative Example 1

Evaluation Results of Inventive Example 2, and Inventive Example 3 and Comparative Example 1

Using the shampoos respectively containing the fragrance compositions of Inventive Example 2, Inventive Example 3 and Comparative Example 1, a bundle of uniform human hair (20 g) was soaked in 50 ml of hot water of 40° C. for 20 minutes to effect its adaptation to the hot water, and then washed with each shampoo (1 g). the bundle of human hair was took out, dehydrated, then rinsed with 100 ml of hot water and dehydrated. Sensory evaluation was carried out on the odor generated from the hair after 1 hour of drying, in the same manner as in Inventive Example 1.

As a result, a natural, rich and fresh muskiness which can be found in natural musk, which is also excellent in diffusiveness and voluminousness, was able to given to the fragrance composition and shampoo, prepared based on the formulation of Inventive Example 2, that contain the (R)-form/(S)-form (92.5:7.5) mixture of optically active muscone. In addition, a creamy muskiness having a soft cleanness which leads to whiteness and having excellent powderiness was able to given to the fragrance composition and shampoo, prepared based on the formulation of Inventive Example 3, that contain the (R)-form/(S)-form (77.5:22.5) mixture of optically active muscone. On the other hand, the fragrance composition and shampoo, prepared based on the formulation of Comparative Example 1, which contain (R)-muscone (100%), were weak in diffusiveness, and voluminousness and also powderiness, merely giving a flat muskiness.

Inventive Example 4

Production of Fragrance Composition for Body Shampoo

A fragrance composition for body shampoo was prepared in the usual way based on the following formulation.

Formulation Example 2

| Components | Part(s) by weight |
| --- | --- |
| Lemon oil | 100 |
| Lime oil | 180 |
| Geranyl nitrile | 10 |
| Aldehyde C-8 10% DPG solution | 25 |
| Aldehyde C-10 10% DPG solution | 35 |
| Ethyl decanoate | 12 |
| Triplal (mfd. by IFF) | 3 |
| Isocyclocitral 10% DPG solution | 25 |
| Styralyl acetate | 20 |
| α-Terpineol | 30 |
| Linalool | 70 |
| Linalyl acetate | 50 |
| Geraniol | 60 |
| Geranyl acetate | 5 |
| Lilial (mfd. by Givaudan) | 80 |
| Hexyl cinnamic aldehyde | 120 |
| Myrac aldehyde (mfd. by IFF) | 15 |
| Cis-3-hexenyl salicylate | 15 |
| β-Ionone | 25 |
| Heliotropine | 5 |
| Tonalid (mfd. by PFW) | 30 |
| (R)-form/(S)-form (92.5:7.5) mixture of optically active muscone | 5 |
| Dipropylene glycol | Balance |
| Total | 1000 |

Inventive Example 5

A fragrance composition for body shampoo was prepared by the same formulation of Inventive Example 4, except that an (R)-form/(S)-form (77.5:22.5) mixture of optically active muscone was used instead of the (R)-form/(S)-form (92.5:7.5) mixture of optically active muscone in the formulation of Inventive Example 4.

Comparative Example 2

A fragrance composition for body shampoo use was prepared by the same formulation of Inventive Example 4, except that (R)-muscone (100%) was used instead of the (R)-form/(S)-form (92.5:7.5) mixture of optically active muscone in the formulation of Inventive Example 4.

Application Example 2

Production of Body Shampoo

Body shampoos were prepared using the fragrance compositions for body shampoo prepared in Inventive Example 4, Inventive Example 5 and Comparative Example 2.

| Body shampoo composition | (% by weight) |
| --- | --- |
| Dibutylhydroxytoluene | 0.05 |
| Methyl paraben | 0.10 |
| Propyl paraben | 0.10 |
| Tetrasodium edetate | 0.10 |
| Potassium chloride | 0.20 |
| Glycerol | 5.00 |
| Coconut oil fatty acid diethanolamide (2) | 3.00 |
| Polyoxyethylene lauryl ether sodium acetate (3 E.O.) (30%) | 10.00 |
| Coconut oil fatty acid amide propyl betaine liquid (34%) | 25.00 |
| Potassium myristate (40%) | 25.00 |
| Fragrance composition* | 0.50 |
| Purified water | balance |
| Total | 100.00 |

*Fragrance composition of Inventive Example 4, Inventive Example 5 or Comparative Example 2

Evaluation Results of Inventive Example 4, Inventive Example 5 and Comparative Example 2

Using body shampoos containing the fragrance compositions of Inventive Example 4, Inventive Example 5 and Comparative Example 2, the palm of hand was washed with 50 ml of hot water of 40° C., and then washed with each body shampoo (1 g). After rinsing with 100 ml of hot water, the moisture was wiped out using a dry towel. At that time, sensory evaluation was carried out on the odor generated from the palm of hand in the same manner as in Inventive Example 1.

As a result, a natural, rich and fresh muskiness which can be found in natural musk, which is also excellent in diffusiveness and voluminousness, was able to given to the fragrance composition and shampoo, prepared based on the formulation of Inventive Example 4, that contain the (R)-form/(S)-form (92.5:7.5) mixture of optically active muscone. A creamy muskiness having a soft cleanness which leads to whiteness and having excellent powderiness was able to given to the fragrance composition and shampoo, prepared based on the formulation of Inventive Example 5, that contain the (R)-form/(S)-form (77.5:22.5) mixture of optically active muscone. On the other hand, the fragrance composition and shampoo, prepared based on the formulation of Comparative Example 2, which contain (R)-muscone (100%), were weak in diffusiveness, and voluminousness and also powderiness, merely giving a flat muskiness.

Inventive Example 6

Production of Fragrance Composition for Perfume

A fragrance composition for perfume was prepared in the usual way based on the following formulation.

Formulation Example 3

| Components | Part(s) by weight |
| --- | --- |
| α-Pinene | 8 |
| Aldehyde C-16 | 1 |
| Furylamyl glycolate | 1 |
| Ambrettolide (mfd. by IFF) | 8 |
| Bergamot oil | 15 |

-continued

| Components | Part(s) by weight |
|---|---|
| Carbitol | 100 |
| Cardamom oil | 3 |
| L-citronellol | 30 |
| β-Damascone | 2 |
| Dimethyloctanol 10% DPG solution | 4 |
| Dipropylene glycol | 29 |
| Dynascone 10% DPG solution | 5 |
| Ethyl acetate 10% DPG solution | 4 |
| Ethyl acetoacetate | 15 |
| Galbanum oil 10% DPG solution | 10 |
| Hedione (mfd. by Firmenich) | 180 |
| Heliobouquet (mfd. by Takasago International Corporation) | 10 |
| Cis-3-hexenol | 2 |
| Cis-3-hexenol 10% DPG solution | 3 |
| β-Ionone | 10 |
| Jasmine absolute | 3 |
| Lime oil 10% DPG solution | 5 |
| Linalyl acetate | 40 |
| 8-Mercaptomenthone 10% DPG solution | 8 |
| Musk T (mfd. by Takasago International Corporation) | 200 |
| Nerolidol | 46 |
| Phenylethyl alcohol | 17 |
| β-Pinene | 117 |
| Rhubofix (mfd. by Firmenich) | 12 |
| Rose absolute | 3 |
| Rose oil 10% DPG solution | 5 |
| 1-Rose oxide 10% DPG solution | 15 |
| Santalex T (mfd. by Takasago International Corporation) | 40 |
| Triplal (mfd. by IFF) | 14 |
| Veloutone (mfd. by Firmenich) | 12 |
| Maltol | 5 |
| (R)-form/(S)-form (92.5:7.5) mixture of optically active muscone | 5 |
| Dipropylene glycol | balance |
| Total | 1000 |

Inventive Example 7

A fragrance composition for perfume was prepared by the same formulation of Inventive Example 6, except that an (R)-form/(S)-form (77.5:22.5) mixture of optically active muscone was used instead of the (R)-form/(S)-form (92.5:7.5) mixture of optically active muscone in the formulation of Inventive Example 6.

Comparative Example 3

A fragrance composition for perfume was prepared by the same formulation of Inventive Example 6, except that (R)-muscone (100%) was used instead of the (R)-form/(S)-form (92.5:7.5) mixture of optically active muscone in the formulation of Inventive Example 6.

Application Example 3

Production of Facial Cream

Facial creams were prepared using the fragrance compositions for perfume prepared in Inventive Example 6, Inventive Example 7 and Comparative Example 3.

| Facial cream | |
|---|---|
| Components | Weight % |
| Stearyl alcohol | 6.0 |
| Stearic acid | 2.0 |
| Hydrogenated lanolin | 4.0 |
| Squalane | 9.0 |
| Octyl decanol | 10.0 |
| Glycerol | 6.0 |
| Polyethylene glycol | 4.0 |
| Polyoxyethylene (25) cetyl ether | 3.0 |
| Glycerol monostearate | 2.0 |
| Methyl paraben | proper quantity |
| Ethyl paraben | proper quantity |
| Fragrance composition* | 0.1 |
| Purified water | balance |
| Total | 100.0 |

*Fragrance composition of Inventive Example 6, Inventive Example 7 or Comparative Example 3

Evaluation Results of Inventive Example 46, Inventive Example 7 and Comparative Example 3

The facial cream of Comparative Example 3 was applied to the back of left hand, and the same amount of the facial cream of Inventive Example 6 or Inventive Example 7 was applied to the back of right hand. Immediately after the application and 3 hours thereafter, sensory evaluation was carried out on the odor remained on the hand in the same manner as in Inventive Example 1.

As a result, a natural, rich and fresh muskiness which can be found in natural musk, which is also excellent in diffusiveness and voluminousness, was able to given to the fragrance composition and facial cream, prepared based on the formulation of Inventive Example 6, that contain the (R)-form/(S)-form (92.5:7.5) mixture of optically active muscone. A creamy muskiness having a soft cleanness which leads to whiteness and having excellent powderiness was able to given to the fragrance composition and facial cream, prepared based on the formulation of Inventive Example 7, that contain the (R)-form/(S)-form (77.5:22.5) mixture of optically active muscone. On the other hand, the fragrance composition and facial cream, prepared based on the formulation of Comparative Example 3, which contain (R)-muscone (100%), were weak in diffusiveness, and voluminousness and also powderiness, merely giving a flat muskiness.

Inventive Example 8

Production of Fragrance Composition for Detergent

A fragrance composition for detergent was prepared in the usual way based on the following formulation.

Formulation Example 4

| Components | Part(s) by weight |
|---|---|
| p-t-Butylcyclohexyl acetate | 10 |
| Acetyl cedrene | 10 |
| Egizarutolid | 5 |
| Galaxolide 50 BB* (mfd. By IFF) | 15 |
| Hexadecanolide | 1 |

-continued

| Components | Part(s) by weight |
|---|---|
| β-Ionone | 10 |
| Orubiton (manufactured by Takasago International Corporation) | 8 |
| Musk T (manufactured by Takasago International Corporation) | 14 |
| Patchouli alcohol | 5 |
| Vetivelyl acetate | 5 |
| Hedione (mfd. by Firmenich) | 6 |
| Triplal (mfd. by IFF) | 6 |
| (R)-form/(S)-form (92.5:7.5) mixture of optically active muscone | 5 |
| Total | 100 |

Inventive Example 9

A fragrance composition for detergent was prepared by the same formulation of Inventive Example 8, except that an (R)-form/(S)-form (77.5:22.5) mixture of optically active muscone was used instead of the (R)-form/(S)-form (92.5:7.5) mixture of optically active muscone in the formulation of Inventive Example 8.

Comparative Example 4

A fragrance composition for detergents was prepared by the same formulation of Inventive Example 8, except that an optically active muscone (R)-muscone (100%) was used instead of the (R)-form/(S)-form (92.5:7.5) mixture of optically active muscone in the formulation of Inventive Example 8.

Application Example 4

Preparation of Powdered Detergent

Powdered detergents were prepared using the fragrance compositions for detergent prepared in Inventive Example 8, Inventive Example 9 and Comparative Example 4.

| Powdered detergent composition | |
|---|---|
| Components | Weight % |
| $C_{14-15}$ alkylethoxysulfonic acid | 5.5 |
| $C_{12-13}$ straight chain alkylsulfonic acid | 12.7 |
| $C_{12-13}$ alkyl ethoxylate | 0.5 |
| Aluminosilicate (76%) | 25.4 |
| Soap | 3.0 |
| zeolite | 23.0 |
| Sodium silicate | 1.0 |
| Sodium carbonate | balance |
| Sodium sulfate | 4.0 |
| Sodium sulfite | 1.0 |
| Enzyme | 1.0 |
| Acrylic acid maleic acid copolymer | 2.5 |
| Fluorescent dye | 0.3 |
| Silicone | 0.3 |
| Fragrance composition* | 0.3 |
| Moisture | 3.0 |
| Total | 100.0 |

*Fragrance composition of Inventive Example 8, Inventive Example 9 or Comparative Example 4

Evaluation Results of Inventive Example 8, Inventive Example 9 and Comparative Example 4

Using powdered detergents containing the fragrance compositions of Inventive Example 8, Inventive Example 9 and Comparative Example 4, a towel was washed and subjected to dehydration treatment. At that time, sensory evaluation was carried out on the odor generated from the towel in the same manner as in Inventive Example 1. As a result, a natural, rich and fresh muskiness which can be found in natural musk, which is also excellent in diffusiveness and voluminousness, was able to given to the fragrance composition and powdered detergent, prepared based on the formulation of Inventive Example 8, that contain the (R)-form/(S)-form (92.5:7.5) mixture of optically active muscone. A creamy muskiness having a soft cleanness which leads to whiteness and having excellent powderiness was able to given to the fragrance composition and powdered detergent, prepared based on the formulation of Inventive Example 9, that contain the (R)-form/(S)-form (77.5:22.5) mixture of optically active muscone. On the other hand, the fragrance composition and powdered detergent, prepared based on the formulation of Comparative Example 4, which contain (R)-muscone (100%), were weak in diffusiveness, and voluminousness and also powderiness, merely giving a flat muskiness.

Inventive Example 10

Production of Fragrance Composition for Softener

A fragrance composition for detergent was prepared in the usual way based on the following formulation.

Formulation Example 5

| Components | Part(s) by weight |
|---|---|
| L-citronellol | 19.3 |
| γ-Methyl ionone | 10.0 |
| Orubiton (manufactured by Takasago International Corporation) | 10.0 |
| Lilial (mfd. by Givaudan) | 20.0 |
| β-Ionone | 5.0 |
| Vanillin | 0.5 |
| Raspberry ketone | 0.2 |
| Acetyl cedrene | 15.0 |
| Hexyl cinnamic aldehyde | 18.3 |
| Linalool | 1.0 |
| Hexyl salicylate | 0.2 |
| (R)-form/(S)-form (92.5:7.5) mixture of optically active muscone | 0.5 |
| Total | 100.0 |

Inventive Example 11

A fragrance composition for softener was prepared by the same formulation of Inventive Example 10, except that an (R)-form/(S)-form (77.5:22.5) mixture of optically active muscone was used instead of the (R)-form/(S)-form (92.5:7.5) mixture of optically active muscone in the formulation of Inventive Example 10.

Comparative Example 5

A fragrance composition for softener was prepared by the same formulation of Inventive Example 10, except that an optically active muscone (R)-muscone (100%) was used instead of the (R)-form/(S)-form (92.5:7.5) mixture of optically active muscone in the formulation of Inventive Example 10.

Application Example 2

Production of Body Shampoo

Powdered detergents were prepared using the fragrance compositions for softener prepared in Inventive Example 10, Inventive Example 11 and Comparative Example 5.

| Softener composition for clothing use | (Weight %) |
|---|---|
| Dialkyldimethylammonium chloride | 15.0 |
| POE (30) lauryl ether | 3.0 |
| Fatty acid | 1.0 |
| dimethyl polysiloxane | 0.5 |
| Ethylene glycol | 5.0 |
| Antiseptic | proper quality |
| Sequestering agent | proper quality |
| Fragrance composition* | 0.3 |
| Ion exchange water | balance |
| Total | 100.0 |

*Fragrance composition of Inventive Example 10, Inventive Example 11 or Comparative Example 5

Evaluation Results of Inventive Example 10, Inventive Example 11 and Comparative Example 5

Using softeners for clothing use containing the fragrance compositions of Inventive Example 10, Inventive Example 11 and Comparative Example 5, a towel washed with a perfume-free detergent was soaked therein for 10 minutes and then subjected to a dehydration treatment. At that time, sensory evaluation was carried out on the odor generated from the towel in the same manner as in Inventive Example 1. As a result, a natural, rich and fresh muskiness which can be found in natural musk, which is also excellent in diffusiveness and voluminousness, was able to given to the fragrance composition and powdered detergent, prepared based on the formulation of Inventive Example 10, that contain the (R)-form/(S)-form (92.5:7.5) mixture of optically active muscone. A creamy muskiness having a soft cleanness which leads to whiteness and having excellent powderiness was able to given to the fragrance composition and powdered detergent, prepared based on the formulation of Inventive Example 11, that contain the (R)-form/(S)-form (77.5:22.5) mixture of optically active muscone. On the other hand, the fragrance composition and powdered detergent, prepared based on the formulation of Comparative Example 5, which contain (R)-muscone (100%), were weak in diffusiveness, and voluminousness and also powderiness, merely giving a flat muskiness.

Based on the above descriptions, the invention can also be described as follows.

(1) A fragrance composition, comprising an optically active muscone as the active ingredient, which is a mixture of (R)-form of optically active muscone and (S)-form of optically active muscone, in which their mixing ratio is within the range of from 90:10 to 95:5 in terms of weight ratio.

(2) A fragrance composition, comprising an optically active muscone as the active ingredient, which is a mixture of (R)-form of optically active muscone and (S)-form of optically active muscone, in which their mixing ratio is within the range of from 75:25 to 80:20 in terms of weight ratio.

(3) A fragrance enhancer for fragrances or cosmetics, comprising an optically active muscone as the active ingredient, which is a mixture of (R)-form of optically active muscone and (S)-form of optically active muscone, in which their mixing ratio is within the range of from 90:10 to 95:5 in terms of weight ratio.

(4) A fragrance enhancer for fragrances or cosmetics, comprising an optically active muscone as the active ingredient, which is a mixture of (R)-form of optically active muscone and (S)-form of optically active muscone, in which their mixing ratio is within the range of from 75:25 to 80:20 in terms of weight ratio.

(5) An additive agent for enhancing a fragrance in fragrances or cosmetics, which is a mixture of (R)-form of optically active muscone and (S)-form of optically active muscone, in which their mixing ratio is within the range of from 90:10 to 95:5 in terms of weight ratio.

(6) An additive agent for enhancing a fragrance in fragrances or cosmetics, which is a mixture of (R)-form of optically active muscone and (S)-form of optically active muscone, in which their mixing ratio is within the range of from 75:25 to 80:20 in terms of weight ratio.

(7) A fragrance composition containing the additive agent described in the aforementioned (5) or (6) at a concentration of from 0.001 to 20% by weight.

(8) Use of an optically active muscone composition, in which the ratio of (R)-form of optically active muscone to (S)-form of optically active muscone is from 90:10 to 95:5 in terms of weight ratio, as a fragrance enhancer for fragrances or cosmetics for adding a musky odor to fragrances or cosmetics.

(9) Use of an optically active muscone composition, in which the ratio of (R)-form of optically active muscone to (S)-form of optically active muscone is from 75:25 to 80:20 in terms of weight ratio, as a fragrance enhancer for fragrances or cosmetics for imparting a musky odor to fragrances or cosmetics.

The invention claimed is:

1. A method of enhancing fragrance, comprising the steps of adding to a cosmetic from 0.0001 to 10% by weight of an optically active muscone composition which comprises (R)- and (S)-forms of optically active muscone, wherein the weight ratio of said (R)- and (S)-forms of optically active muscone in said optically active muscone composition is from 90:10 to 95:5, respectively.

2. A method of enhancing fragrance, comprising the steps of adding to a cosmetic from 0.0001 to 10% by weight of an optically active muscone composition which comprises (R)- and (S)-forms of optically active muscone, wherein the weight ratio of said (R)- and (S)-forms of optically active muscone in said optically active muscone composition is from 75:25 to 80:20, respectively.

3. The method according to either of claim 1, or 2, wherein the cosmetic contains from 0.001 to 5% by weight of said optically active muscone composition.

4. The method according to claim 3, wherein said cosmetic contains from 0.01 to 1% by weight of said optically active muscone composition.

* * * * *

UNITED STATES PATENT AND TRADEMARK OFFICE
CERTIFICATE OF CORRECTION

| | | |
|---|---|---|
| PATENT NO. | : 8,093,203 B2 | Page 1 of 3 |
| APPLICATION NO. | : 11/719109 | |
| DATED | : January 10, 2012 | |
| INVENTOR(S) | : Kenichi Yamamoto et al. | |

It is certified that error appears in the above-identified patent and that said Letters Patent is hereby corrected as shown below:

COLUMN 1:

Line 18, "to be referred sometimes to" should read --sometime referred to--;
    Line 33, "highly-scenting" should read --highly-scented--;
    Line 34, "uprush" should read --popularity--;
    Lines 34-35, "style of people" should read --lifestyle--;
    Line 37, "or" (first occurrence) should be deleted;
    Line 39, "ing" should read --ed--;
    Line 40, "imaged characteristically." should read --reflected.--; and
    Line 63, "larger" should read --stronger--.

COLUMN 2:

Line 1, "highly-scenting" should read --highly-scented--;
    Line 25, "highly-scenting" should read --highly-scented--;
    Line 48, "highly-scenting" should read --highly-scented--;
    Line 62, "highly" should read --highly- --; and
    Line 63, "scenting" should read --scented--.

COLUMN 3:

Line 14, "according to claim 1" should be deleted;
    Line 46, "is use of" should read --uses--;
    Line 49, "is use of" should read --uses--;
    Line 60, "these" should read --this--; and
    Line 67, "of" (first occurrence) should be deleted.

Signed and Sealed this
Seventeenth Day of April, 2012

David J. Kappos
*Director of the United States Patent and Trademark Office*

COLUMN 5:

Line 2, "highly-scenting" should read --highly-scented--;
Line 3, "highly" should read --highly- --;
Line 4, "scenting" should read --scented--; and
Line 12, "Amount" should read --The amount--.

COLUMN 6:

Line 2, "Perfum," should read --Parfum,--;
Line 6, "make" should read --makeup--;
Line 6, "as the" (first occurrence) should be deleted;
Line 10, "as the" should be deleted;
Line 14, "as the" (first occurrence) should be deleted;
Line 16, "as the" (first occurrence) should be deleted;
Line 19, "as the" (first occurrence) should be deleted;
Line 21, "as the" (first occurrence) should be deleted;
Line 23, "as the" (first occurrence) should be deleted;
Line 25, "as the" (first occurrence) should be deleted;
Line 29, "as the" (first occurrence) should be deleted;
Line 32, "as the" (first occurrence) should be deleted;
Line 33, "as the" (first occurrence) should be deleted;
Line 36, "as the" (first occurrence) should be deleted;
Line 38, "as the" should be deleted;
Line 42, "as the" (first occurrence) should be deleted;
Line 44, "as the" should be deleted;
Line 47, "as the" (first occurrence) should be deleted; and
Line 53, "like" should read --like,--.

COLUMN 7:

Line 30, "and broadening-less poor and" should read --, and poorly diffusive and--;
Line 47, "followings" should read --following examples--;
Line 53, "followings," should read --following examples,--;
Line 65, "spending" should read --for a period of--; and
Line 67, "spending" should read --for a period of--.

COLUMN 8:

Line 38, "2,15-hexadecanedion" should read --2,15-hexadecanedione--; and
Line 40, "spending" should read --for a period of--.

COLUMN 9:

Line 1, "Ru$_2$Cl4" should read --Ru$_2$Cl$_4$--.

COLUMN 10:

Line 9, "scenting" should read --scented--;
Line 13, "scenting" should read --scented--;
Line 16, "scenting" should read --scented--;
Line 26, "scenting" should read --scented--;
Line 29, "scenting" should read --scented--; and
Line 31, "scenting" should read --scented--.

COLUMN 12:

Line 44, "the" should read --The--;
Line 45, "took" should read --taken--;
Line 53, "able to given" should read --imparted--;
Line 59, "able to" should be deleted; and
Line 60, "given" should read --imparted--.

COLUMN 16:

Line 30, "remained" should read --remaining--;
Line 34, "able to given" should read --imparted--;
Line 39, "able to" should be deleted; and
Line 40, "given" should read --imparted--.

COLUMN 18:

Line 11, "able to given" should read --imparted--.

COLUMN 19:

Line 41, "able to given" should read --imparted--;
Line 46, "able to" should be deleted; and
Line 47, "given" should read --imparted--.